United States Patent [19]

Groat et al.

[11]  4,418,057
[45]  Nov. 29, 1983

[54] METHOD OF FORMING STABLE DENTAL GEL OF STANNOUS FLUORIDE

[75] Inventors: Dennis E. Groat; Richard W. Sell, both of Dallas; Richard J. Kalish, Carrollton; Horace E. Melton, Irving, all of Tex.

[73] Assignee: Scherer Laboratories, Inc., Dallas, Tex.

[21] Appl. No.: 465,107

[22] Filed: Feb. 9, 1983

[51] Int. Cl.$^3$ .................... A61K 7/18; A61K 33/16
[52] U.S. Cl. .................................. 424/151; 424/52
[58] Field of Search ............................ 424/52, 151

[56] References Cited

U.S. PATENT DOCUMENTS

| | | | |
|---|---|---|---|
| 2,751,328 | 6/1956 | Sanders | 424/49 |
| 2,839,448 | 6/1958 | Hager et al. | 424/52 |
| 3,070,510 | 12/1962 | Cooley et al. | 424/52 |
| 3,105,013 | 9/1963 | Saul et al. | 424/52 |
| 3,282,792 | 11/1966 | Fiscella | 424/52 |
| 3,337,412 | 8/1967 | Elbreder | 424/151 |
| 3,892,843 | 7/1975 | Muhler et al. | 424/52 |
| 4,022,881 | 5/1977 | Hawking | 424/52 |
| 4,132,771 | 1/1979 | Schreiber et al. | 424/52 |
| 4,203,966 | 5/1980 | Faunce | 424/52 |
| 4,251,507 | 2/1981 | Olson | 424/49 |
| 4,267,167 | 5/1981 | Weitzman et al. | 424/151 |

*Primary Examiner*—Shep K. Rose
*Attorney, Agent, or Firm*—Emory L. Groff, Jr.

[57] ABSTRACT

A method for producing a stable commercial-scale size batch of a stannous fluoride containing gel comprising admixing predetermined, critical proportions of the ingredients of the gel at critical temperatures in stages designed to stabilize the gel against deterioration in storage.

7 Claims, No Drawings

METHOD OF FORMING STABLE DENTAL GEL OF STANNOUS FLUORIDE

BACKGROUND OF THE INVENTION

Fluorides in a variety of forms have been demonstrated to be of significant value in reducing the occurrence of dental caries. Indeed, recognized authorities in the field of dental care have stated that there are "no bad fluorides" for this purpose.

Fluorides have been found to be best utilized for the prevention of caries when ingested, thus giving rise to the fluoridation of public water supplies. Fluorides are also of value when applied topically. A variety of topical fluoride treatments are provided professionally in the dental office. In addition, fluorides have been provided in commercial toothpastes and dentifrices. Of the fluorides available for topical application, stannous fluoride has proved to be the fluoride of choice due to the fact that the stannous ion combines with the naturally occurring phosphate in the enamel and dentin structure of the tooth to form stannous fluorophosphate which serves as a protective coating on the tooth surface.

Efforts have long been made by the leading commercial toothpaste marketers to make use of stannous fluoride as the source of "dentifrice-fluoride". Recently, however, the leading dentifrice producers have abandoned this effort, due primarily to the cost factor since stannous fluoride is several times as expensive as other available fluorides for the purpose. Moreover, the inherent instability of stannous fluoride in the presence of moisture and its reactivity with abrasives commonly used in dentifrices have contributed to the widespread abandonment of its use. It is difficult, if not impossible, to avoid the exposure of the stannous fluoride to moisture and to the abrasives present in a dentifrice which have a negative effect on the stability of the stannous ion.

Thus, efforts have increased to make stannous fluoride available in a stable and efficacious form in applications other than in toothpaste and dentifrices. For the stannous ion to be of value it must be freely available and not in combination with or locked into other chemical combinations as well as stable. Concentrations of stannous fluoride at a level of 0.1% available stannous ion have been demonstrated to be of value. A 0.4% stannous fluoride preparation has most frequently been demonstrated to be the concentration of choice in the treatment of dental caries.

While topical applications are frequently performed in the dental office there is also a need for follow-up daily application and use by the patient. Thus, "home-care" or "patient-care" availability is desirable. For this purpose a gel with the requisite viscosity to accommodate toothbrush application is the accepted marketable form.

Researchers recently discovered that stannous fluoride is relatively stable in anhydrous glycerin. However, glycerin solutions of stannous fluoride do not lend themselves to topical application to teeth because of their low viscosity. A variety of thickeners have been incorporated in glycerin solutions of stannous fluoride in an effort to increase the viscosity and, hence, the residence time of the composition on teeth when topically applied.

However, as in the case of dentifrices or toothpastes containing moisture and abrasives, the thickening agent used in preparing gels often contributes to the instability of the stannous fluoride. Not only is the choice of thickening agent critical to the stability of the available stannous ion, the technique in the process of making the gel product has been found to be of prime importance. In order to accommodate the demand for a "home-care" type gel, the product must be capable of being produced in quantities sufficiently large to make it economically feasible; i.e., "commercial-size batches" from which smaller consumer-size packages may be formulated.

Thickeners such as sodium carboxy methyl cellulose react with stannous ion thus contributing to the instability of the product. Hydroxyethylcellulose has been suggested for use as a thickener. Careful preparation of a gel under rigorous laboratory conditions employing hydroxyethylcellulose has yielded stable preparations. Under such controlled conditions, factors which contribute to instability are easily kept at a minimum.

Attempts to prepare commercial-size batches of gel with hydroxyethylcellulose economically, however, have consistently met with failure. The processing, mixing, temperature, apparatus, etc. requirements of economically feasible large batch gel production techniques adversely affect the stability of the stannous ion/hydroxyethylcellulose/glycerin system.

It is an object of the present invention to provide a method for the production in commercial-scale size batches of a stable gel containing stannous fluoride, glycerin and hydroxyethylcellulose which is stable over prolonged periods of time against deterioration.

It is a further object of the invention to provide a commercial-scale size batch of a stable gel containing stannous fluoride, glycerin and hydroxyethylcellulose.

SUMMARY OF THE INVENTION

According to the present invention there is provided a method of producing a commercial-scale size batch of stable gel consisting essentially of from about 96% to about 98% of anhydrous glycerin, from about 1.8% to about 2.2% of hydroxyethylcellulose and from about 0.38% to about 0.42% of stannous fluoride wherein the concentration of stannous fluoride in the gel is stable during storage under normal conditions against deterioration to levels below that desired in the use of the gel as a topical treating agent for the prevention of dental caries, the first stage of the method comprising the sequential steps:

(a) dissolving 50% of the stannous fluoride present in the gel in from about 15% to about 18% of the anhydrous glycerin present in the gel at a temperature in the range of from about 150° C. to about 185° C.;

(b) adding a sufficient quantity of anhydrous glycerin to the mixture to reduce the temperature thereof to from about 130° C. to about 150° C.;

(c) dissolving in the mixture 50% of the hydroxyethylcellulose present in the gel; and (d) adding to the mixture sufficient anhydrous glycerin to bring the volume thereof up to about 50% of the volume of the gel; and the second stage of the method comprising repeating the sequential steps of the above first stage and combining the products of the two stages.

The invention also provides a novel commercial-scale size batch of a stannous fluoride containing gel produced according to the above-described method, which gel is stable against deterioration of stannous fluoride levels over prolonged periods of storage.

DETAILED DESCRIPTION OF THE INVENTION

The invention is predicated on the discovery that preparing the gel according to the above-described procedure results in a formulation which is stable for long periods of time and at critical stability periods. Significant deviation from the protocol of the inventive method yields a product gel whose stannous fluoride concentration is rapidly reduced due to interaction with the hydroxyethylcellulose content thereof or from the the stannous fluoride will precipitate.

The invention relates to a dental containing—as an anti-caries topical treatment agent, stannous fluoride with both the stannous and fluoride ions available in a stable, predictable level of concentration. More particularly, it relates to a multi-step compounding and manufacturing procedure involving various combinations of heating, cooling and mixing sequences to produce a stable stannous fluoride dental gel in batch sizes sufficiently large to be of commercial or marketable value. The method of the present invention ameliorates the degradative effects of moisture, oxidation, pH variation, etc. in the stannous ion concentration of the gel.

The product thus produced is a dental gel, i.e., an oral composition designed for use as a topical fluoride treatment featuring the availability of stannous and fluoride ions as its active ingredients and not as a dentifrice containing abrasives designed to clean teeth. The gel is normally recommended for use in addition to and not as a substitute for a dentifrice.

Whereas it was found to be relatively easy to formulate a stable stannous fluoride containing gel based on glycerin and hydroxyethylcellulose in small batch sizes under laboratory conditions where all procedure parameters are subject to rigorous and precise control, the production of commercial-size batches, i.e., approximately 776 kg or one-half size batches thereof, where control must be "process-oriented", i.e., economical and efficient, have consistently yielded unsatisfactory results.

As used herein, "commercial batch-size" is meant to denote an amount that, when proportioned into packaged units, a sufficient number of units is yielded to make the process of manufacturing and packaging economically feasible for commercial distribution.

It should be noted that the determination of the "commercial batch-size" must take into consideration factors other than economic factors, i.e., design of equipment; ability to control quality and consistency; ability to control environmental conditions (exposure to air and moisture); ability to control sensitive steps in the process (mixing times, cooling); ability to handle the process in safety; and the ability to maintain a balanced inventory of finished product so that a line of commercially attractive flavors and sizes can be made readily available.

The present invention enables a solution to this in that there is provided a method which (1) produces a composition which may be sub-divided and properly packaged for home-care use under professional supervision, (2) is of a viscosity so as to permit its use with a toothbrush as an applicator; and (3) is stable as to its stannous fluoride content over extended periods of time, particularly when stored under normal conditions. Further, the composition is of a quality and stability to equal the "laboratory produced compositions" used to clinically establish the efficacy and advantages of stannous fluoride topical fluoride treatment agents having known concentrations. Thus, the invention provides a commercially available composition in terms of quality and stability that will enhance the value of a variety of clinical studies such as (1) the further documentation of the value of stannous fluoride as a topical fluoride treatment for the purpose of reducing the occurrence of dental caries, (2) the further clinical documentation of the value of stannous fluoride in the area of hypersensitivity treatment, and (3) the further clinical documentation of the value of stannous fluoride in the area of plaque control.

In the method of the present invention the first and second stages of the process may be carried out sequentially in the same or different vessels or simultaneously. A typical operation employs a 307 liter working capacity stainless steel compounding tank which is 76.8 cm in diameter and 74.3 cm in height. It is provided with automatic mixer to agitate the contents and also electric immersion heater coils located 58.7 cm from the top of the compounding tank. The coils are of circular configuration 63.5 cm in diameter located 6.7 cm from the tank side wall and 16.5 cm from the bottom. The inner opening of the heater coils' diameter is 48 cm to allow space for mixer agitation. The tank is equipped with an automatic temperature-controlled cut-off. Temperature ranges are tested with a thermometer graduated from 90° to 230° C. having an immersion probe approximately 75 cm in length. The tank enables the preparation of a 776 kg batch of gel.

Glycerin is transferred into the compounding container to a level about 10 cm above the heating coil and heated to 180° C. The stannous fluoride is dissolved in the heated glycerin by mixing for 30–45 minutes. A sufficient quantity of glycerin is added to the batch to bring the temperature thereof to about 135° C. The hydroxyethylcellulose, alone or previously slurried in from about 10% to about 17% of the glycerin present in the final gel, is added to the above mixture, preferably slowly to prevent lumping and the contents of the container mixed until all ingredients are dissolved and a homogeneous solution is obtained. Additional glycerin is added to bring the volume of the mixture up about 13 cm from the top of the tank and the contents thoroughly mixed. The mixture is then transferred to a stainless steel holding tank. The above procedure is then repeated using fresh ingredients and the second batch transferred to the holding tank containing the first batch. The two batches are thoroughly mixed after the addition of a suitable flavoring agent (e.g., creme de menthe, cinnamon, etc.) and other adjuvants at about 80° C. for about 20 minutes.

The final product is ready for packaging or storage without danger of deterioration of the stannous fluoride concentration due to interaction with the hydroxyethylcellulose.

The following non-limiting examples are illustrative of the present invention. In each of the following examples the apparatus described above was employed.

EXAMPLE 1

Glycerin (150 liters) was added to the tank and heated to 180° C. Stannous fluoride (1.6 kg) was added and the contents stirred until completely dissolved. Additional glycerin was added until the temperature of the contents reached 160° C.

Hydroxyethylcellulose (7.8 kg) was slurried in 38 liters of glycerin and the slurry slowly added to the mixture in the tank while stirring. Stirring was continued until the contents of the tank were completely dissolved.

Additional glycerin was added to the tank to bring the level of the contents up to 13 cm from the top of the tank. The mixture was stirred until homogeneous and transferred to the holding tank.

The above procedure was repeated utilizing fresh ingredients and the two batches thoroughly admixed in the holding tank. The final mixture was passed through an 80 mesh screen and packaged.

EXAMPLE 2

Glycerin (100 liters) was added to the compounding tank and heated to 180° C. Stannous fluoride (1.6 kg) was added to the heated glycerin and the mixture stirred for about 15 minutes until completely dissolved. Additional glycerin was added to the batch to bring the temperature to 160°-165° C.

Hydroxyethylcellulose (7.8 kg), previously slurried in 30-40 liters of cold glycerin, was added to the batch slowly with stirring and mixing continued until the contents were completely dissolved (about 15-30 min.). The temperature of the contents at this stage was about 140° C.

Glycerin was added to the tank to bring the volume up to 12 cm from the top of the tank and the contents stirred until thoroughly admixed. The batch was transferred to the holding tank.

The above sequence of steps was repeated with fresh ingredients and the thus produced second batch transferred to the holding tank and thoroughly admixed with the first batch.

After passage through an 80 mesh screen the combined batches were packaged for storage.

EXAMPLE 3

Glycerin (150 liters) was added to the compounding tank and heated to 180° C. Stannous fluoride (3.3 kg) was added and mixing continued until complete dissolution was effected.

Hydroxyethylcellulose (15.5 kg) was slurried in 60 liters of cold glycerin and the slurry slowly added to the tank with stirring. Mixing was continued for about 15-30 minutes until the contents were completely dissolved. The temperature of the batch at this stage was 140° C.

Glycerin was added until the level of the contents reached 12 cm from the top of the tank. The mixture was agitated until homogeneous and pumped to the holding tank.

Glycerin was added to 12 cm from the top of the compounding tank and heated to 70° C. The heated glycerin was transferred to the holding tank containing the above produced stannous fluoride containing batch and the mixture stirred until homogeneous after adding one of the following batches of flavoring agent: grape—2 kg; raspberry/creme de menthe—3.27 kg; cinnamon/creme de menthe—5.04 kg; mixed fruit—2.23 kg; mint—3.88 kg. The mixture was passed through an 80 mesh screen, packaged and stored.

EXAMPLE 4

Glycerin (210 liters) was placed in the compounding tank and heated to 180° C. Stannous fluoride (2.3 kg) was added and the mixture stirred until completely dissolved (15-20 minutes). Hydroxyethylcellulose (5.5 kg) was slurried in 60 liters of glycerin at room temperature and the slurry added slowly to the glycerin solution of stannous fluoride. The mixture was stirred until completely dissolved and the temperature reached 135°-140° C. (about 15 minutes). The mixture was transferred to a stainless steel holding tank (660 liter capacity, 96.5 cm diameter × 87 cm Ht.).

Glycerin at 20°-25° C. was added to the mixture until the level of contents was 6.5 cm from the top of the tank. The temperature of the mixture at this stage is 70°-80° C.

Various flavors (2-5 kg) were added and the mixture stirred for 20 minutes, filtered through an 80 mesh screen and packaged for storage.

Each of the products of Examples 1-4 were found to be stable as to stannous fluoride concentrations for at least up to six months.

We claim:

1. A method for producing a commercial-scale size batch of a stable gel consisting essentially of from about 96% to about 98% of anhydrous glycerin, from about 1.8% to about 2.2% of hydroxyethyl cellulose and from about 0.38% to about 0.43% of stannous fluoride wherein the concentration of stannous fluoride in said gel is stable during storage against deterioration to levels below that enabling the use of said gel as a topical treating agent for the prevention of dental caries, the first stage of said method comprising the sequential steps:

(a) dissolving 50% of the stannous fluoride present in said gel from about 15% to about 18% of the anhydrous glycerin present in said gel at a temperature in the range of from about 150° C. to about 180° C.;

(b) adding a sufficient quantity of anhydrous glycerin to said mixture to reduce the temperature thereof of from about 130° C. to about 150° C.;

(c) dissolving in said mixture 50% of the hydroxyethyl cellulose present in said gel; and (d) adding to said mixture sufficient anhydrous glycerin to bring the volume thereof up to about 50% of the volume of said gel; and the second stage of said method comprising repeating the said sequential steps of said first stage and combining the product of said second stage with the product of said first stage.

2. The method of claim 1 wherein said first and second stages are carried out simultaneously.

3. The method of claim 1 wherein said first and second stages are carried out sequentially.

4. The method of claim 1 including the step of adding a flavoring agent to the product produced by combining the respective products of said first and second stages.

5. The method of claim 1 wherein said hydroxyethyl cellulose in said first and/or second stage is slurried in from about 8% to about 12% of the anhydrous glycerin present in said gel prior to addition to said mixture of stannous fluoride and anhydrous glycerin.

6. The method of claim 1 including the step of packaging the said gel.

7. The gel produced according to the method of claim 1.

* * * * *